United States Patent [19]

Scanlon

[11] Patent Number: 4,721,000

[45] Date of Patent: Jan. 26, 1988

[54] AXIAL LOADING MATERIAL TESTING

[75] Inventor: David W. Scanlon, Rehoboth, Mass.

[73] Assignee: Instron Corporation, Canton, Mass.

[21] Appl. No.: 909,271

[22] Filed: Sep. 19, 1986

[51] Int. Cl.[4] .......................... G01N 3/08; G01N 3/02

[52] U.S. Cl. ........................................ 73/833; 73/859; 73/860; 73/857

[58] Field of Search ................. 73/826, 827, 830, 831, 73/833, 834, 818, 819, 821, 822, 825, 796, 797, 798, 856, 857, 859, 860; 279/1 J, 1 L, 1 TE; 269/139, 149

[56] References Cited

U.S. PATENT DOCUMENTS

| | | | |
|---|---|---|---|
| 2,447,660 | 8/1948 | Miklowitz | 73/859 |
| 2,702,929 | 3/1955 | Laddon et al. | 73/859 |
| 2,908,163 | 10/1959 | McClelland | 73/859 |
| 3,005,336 | 10/1981 | Wyman | 73/860 |
| 4,073,185 | 2/1978 | Griffin | 73/859 |

FOREIGN PATENT DOCUMENTS

| | | | |
|---|---|---|---|
| 1903042 | 1/1969 | Fed. Rep. of Germany | 73/856 |
| 2028030 | 12/1971 | Fed. Rep. of Germany | 73/833 |
| 3316218 | 11/1984 | Fed. Rep. of Germany | 73/856 |
| 2270976 | 12/1975 | France | 279/1 L |
| 0002531 | 1/1981 | Japan | 73/856 |
| 0142542 | 9/1982 | Japan | 73/857 |
| 0567992 | 8/1977 | U.S.S.R. | 73/859 |

OTHER PUBLICATIONS

Advanced Technical Data, Bulletin, MTS Div., 1965.

*Primary Examiner*—Stewart J. Levy
*Assistant Examiner*—Robert R. Raevis

[57] ABSTRACT

A grip for a material testing load frame including a grip plate for engaging the end of an elongated sample having a longitudinal axis and a grip body having one end for connecting to the grip plate and another end for connecting to a loading component of the frame, a mechanism for adjusting the concentricity of the plate with respect to the body, and a mechanism for adjusting the angle of the plate with respect to the body, so that when the sample end is engaged by the plate, and the grip body is connected to the loading component, the longitudinal axis and the axis of the loading component can be aligned with respect to the concentricity and angle.

22 Claims, 3 Drawing Figures

AXIAL LOADING MATERIAL TESTING

FIELD OF THE INVENTION

The invention relates to axial loading material testing.

BACKGROUND OF THE INVENTION

Stress/strain and other material strength characteristics of an elongated sample of material are measured in a load frame by engaging a sample at its two ends by grips which apply compressive or tensile loads or both along the longitudinal axis of the sample (axial loading).

It is difficult to get the sample perfectly aligned with the two grips, resulting in uneven loading of the sample (e.g., a 5 to 7% difference in stress at different locations across a cross-sectional slice of a sample). Uneven loading in metal samples causes them to bend, tending to redistribute the stress over a larger area and to reduce the effect on test results of uneven loading. Ceramics, however, are brittle and may crack before desired test loads have been applied.

The typical testing of ceramics involves using a "bend test" in which an elongated, rectangular cross-section sample is supported from below at its ends, and a downward force is applied to the middle, placing the top in compression and the bottom in tension. A limitation of this test for ceramics relates to the cause of failure of ceramics, namely a crack initiated at one of a plurality of flaws within the material when that flaw is subjected to sufficiently high stress. In the bend test only the surface region across the middle of the bottom of the sample is subjected to the highest tensile stress, and there is a smaller probability that a critically sized flaw will be present there. The bend tests can thus give ultimate stress values that are higher than they should be, making them unreliable. With axial loading, on the other hand, the maximum stress is applied uniformly (subject to what was said above about uneven loading) across the width of the entire sample and over its entire length, making it virtually certain that a flaw, wherever located, will be subjected to the maximum stress.

SUMMARY OF THE INVENTION

My invention features a grip that is adjustable to accurately align a test sample with respect to the direction of application of the axial loading force of a test frame. The grip includes a grip plate that engages the sample and is adjustably connected to a grip body, which is in turn connected to the loading component of the test frame. The connection between the plate and the body is adjustable for both concentricity (i.e., the relative positions of the plate and body in a plane perpendicular to the direction of axial loading) and angle. The resulting alignment is sufficiently accurate to permit tensile and compressive axial testing of ceramic samples.

In preferred embodiments, the concentricity adjustment is made using two pairs of opposed adjustment bolts along axes in a plane perpendicular to the loading direction; the angle between the plate and the grip body is adjusted by adjusting four bolts that are parallel to the loading direction; an enlarged end of the sample sits in two wedge pieces (a split conical piece with an axial passage conforming to the shape of the sample end) and is pushed from behind by a piston-driven, hemispherically-shaped piece of ceramic, providing preloading that is maintained during tension/compression testing; and the grip is used with a similar grip on a load frame equipped with a hydrostatic bearing on top of the table to assist in accurate alignment.

Other advantages and features of the invention will be apparent from the following description of a preferred embodiment thereof and from the claims.

DESCRIPTION OF THE PREFERRED EMBODIMENT

The preferred embodiment will now be described.

Drawings

STRUCTURE

Figure 1:
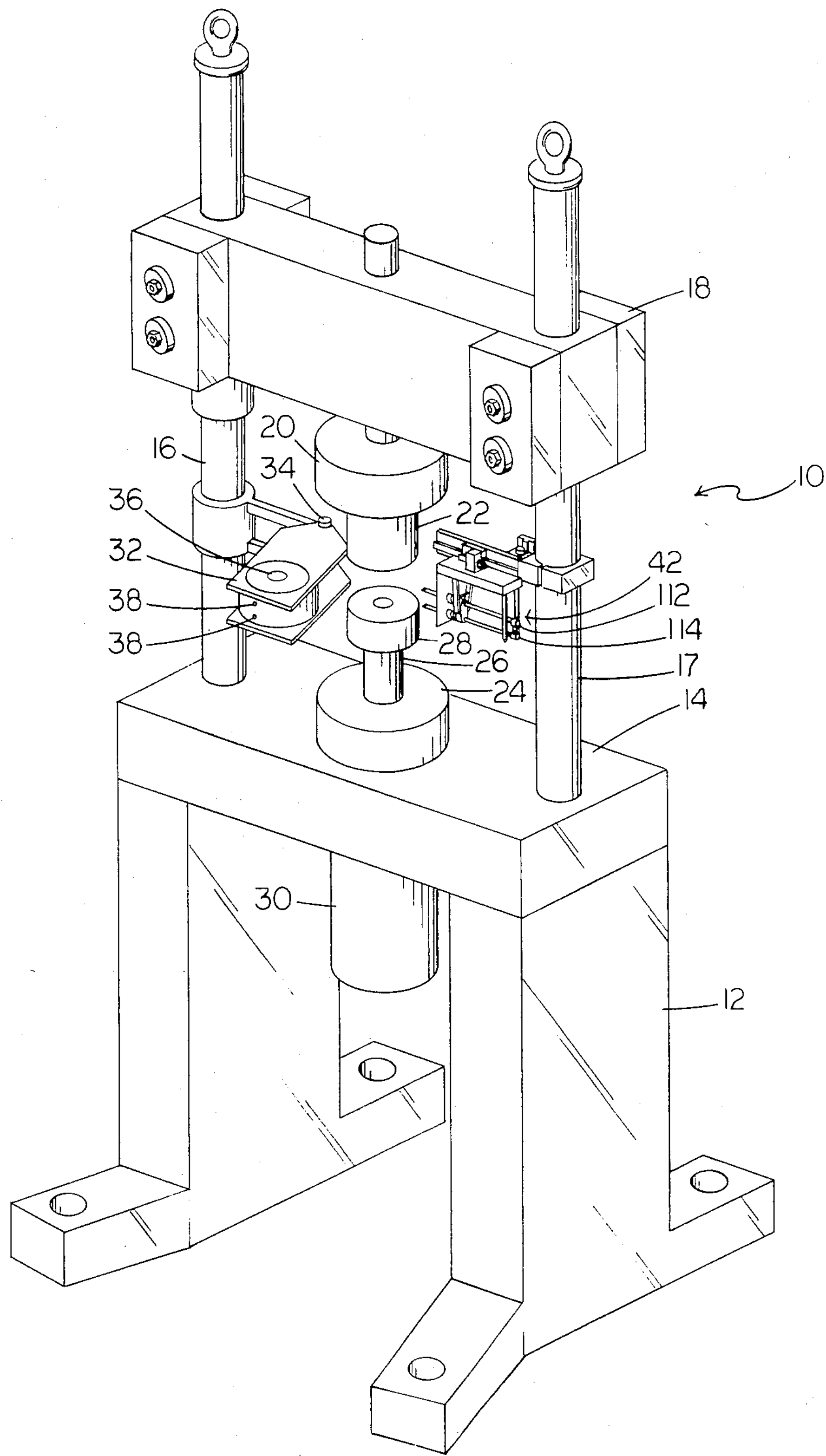
FIG. 1 is a perspective view of a material testing load frame according to the invention.

Referring to FIG. 1, there is shown material testing load frame 10 including feet 12, table 14, vertical columns 16, 17 extending upwardly from table 14, and crosshead 18 between columns 16, 17. Connected to crosshead 18 are load cell 20 and upper grip 22, for gripping the upper end of a sample under test. Directly therebelow and supported by table 14 are hydrostatic bearing 24, actuator rod 26, and lower grip 28, for gripping the lower end of a sample. Actuator 30 is supported below table 14 and drives rod 26, which passes through a hole through table 14. Supported on column 16 is 1500° C. furnace 32, which is pivotally mounted about pivot 34 so as to be movable from the standby position shown in FIG. 1 to an operating position between grips 22, 28. Furnace 32 has central bore 36 for receiving the elongated sample under test and two horizontal passages 38 leading to bore 36 for receiving fingers 112, 114 of extensometer assembly 42, supported by column 17.

Figure 2:
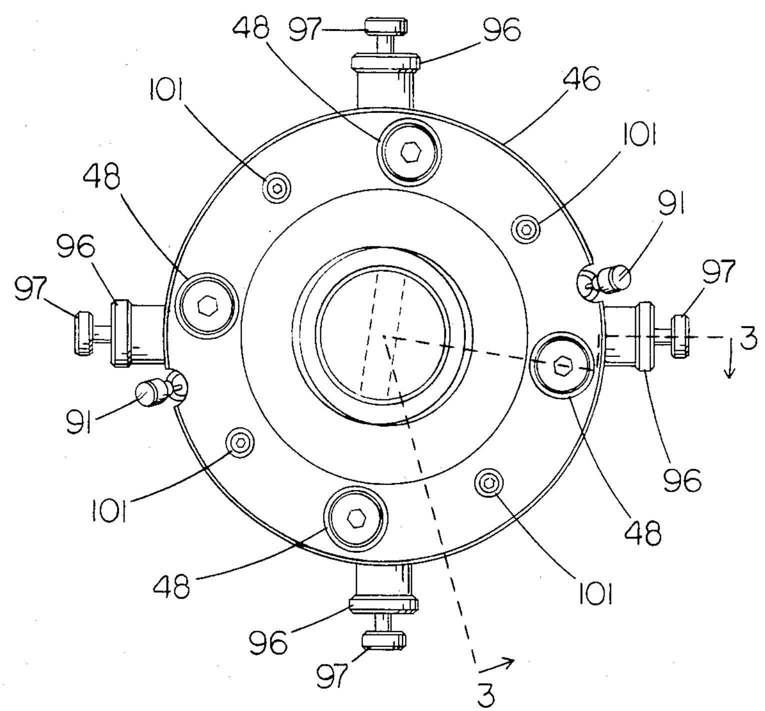
FIG. 2 is a plan view of a grip of the FIG. 1 load frame.
Figure 3:
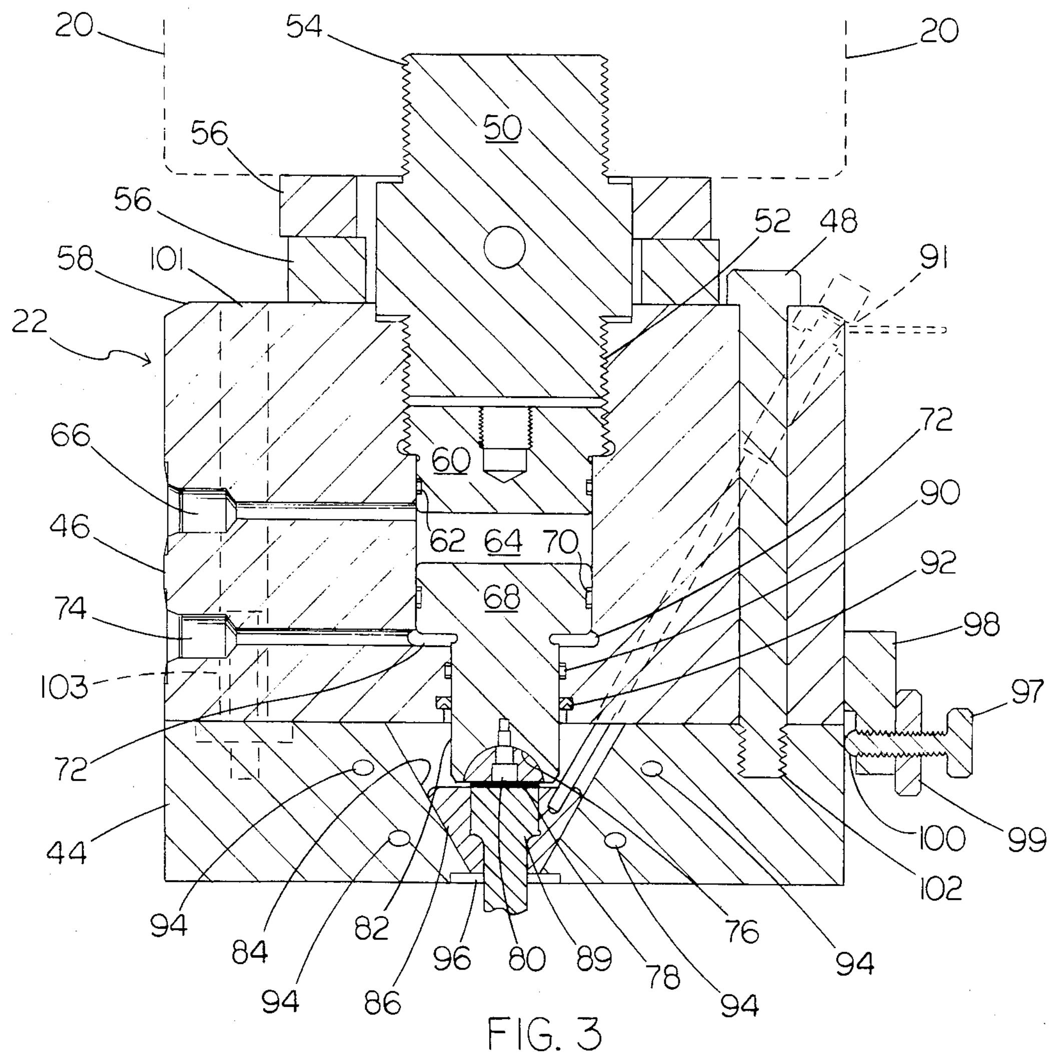
FIG. 3 is a vertical sectional view, taken at 3—3 of FIG. 2, of the FIG. 2 grip.

Referring to FIGS. 2-3, there is shown upper grip 22; lower grip 28 has the identical structure. Grip 22 includes grip plate 44 and grip body 46 secured to plate 44 via four angle adjustment bolts 48, the angle adjusting function of which is described below.

Attachment stud 50, for attaching grip body 46 to load cell 20 (shown in phantom in FIG. 3 and not drawn to scale), has threaded extension 52 securing it into grip body 46. Stud 50 also has threaded extension 54 for making the threaded connection to load cell 20. Wedge washers 56 are provided between load cell 20 and upper surface 58 of grip body 46 to provide a backlash free connection between load cell 20 and body 46.

Below extension 52, plug 60 is threaded into body 46 and contains sealing ring 62 to seal off the upper end of pressure chamber 64. Pressure passage 66 leads to pressure chamber 64. Piston 68 is slidably mounted in the lower portion of chamber 64 and has sealing ring 70 to provide a fluid-tight seal to the chamber. Downward-facing outer annular surface 72 of piston 68 communicates with second pressure passage 74. Around lower extension 82 of piston 68 are sealing ring 90, to provide a seal, and wiper ring 92, to keep out debris. Lower extension 82 of piston 68 has hemispherically-shaped recess 76 for receiving hemispherically-shaped ceramic piece 78 connected to piston 68 via screw 80. The passage in piece 78 in which screw 80 is located is larger than screw 80, permitting slight rotational movement of ceramic piece 78 so that its flat surface automatically rotates to the position of the flat end of a sample.

Lower extension 82 of piston 68 is received in conical recess 84 of grip plate 44 in which two wedge pieces 86 are located. The outer surfaces of wedge pieces 86 have a conical shape, and the inner surfaces of wedge pieces 86 conform to the shape of the outer surface of the enlarged end of the sample 88. Connected to each wedge piece 86 is a spring-biased withdrawing member 91, to assist in mounting a sample in grip 22. Passages 94 in plate 44 receive cooling water. Recess 96 in the lower surface of plate 44 is to receive a fixture for initial alignment of the plates of upper grip 22 and lower grip 28.

Four concentricity adjustment knobs 97 are threaded into overhanging support 98, connected to grip body 46, and have ends 100 bearing against the outer surface of grip plate 44 and locking nuts 99. Angle adjustment bolts 48 have ends 102 received in threaded holes in grip plate 44 and are placed in tension to provide pulling between plate 44 and body 46. Locking bolts 101 mate with threads 103 in the lower end of body 46 and are placed in compression to provide to pushing between plate 44 and body 46, acting to lock adjustment bolts 48 in place.

OPERATION

In operation, a ceramic sample is loaded into frame 10 by first inserting it into bore 36 of furnace 32 while furnace 32 is in the standby position shown in FIG. 1. The heater and sample (wired with strain gages, not shown, at four locations around its midsection and two locations above and two locations below its midsection) are swung into position between grips 22, 28. The upper enlarged end 89 of sample 88 is secured to grip 22 first by placing it within wedge pieces 86, which are pulled back using withdrawing members 91 when the enlarged end is first inserted into conical recess 84. Actuator 30 then pushes lower grip 28 upward into position, and lower grip 28 is connected in the same manner.

The concentricity and angle of grips 22, 28 with respect to the sample are then adjusted to accurately align the sample with the loading forces applied by frame 10. This is done by placing sample 88 under light loads and sensing the strain that the light loads cause using the sensors around sample 120. When it appears that the strains (and thus the stresses) on sample 88 are uneven, concentricity adjustment knobs 96 and angular adjustment bolts 48 are adjusted accordingly. Tensile loads only are used during initial adjustment, and thereafter both tensile and compressive loads are used. When compressive loads are applied, pressure in chamber 64 is applied through piston 68 to the end surface of the sample 88 to lock the position of plate 44 with respect to body 46. After the sample has been properly aligned, locking bolts 101 are similarly turned in compression to act against bolts 48 and maintain the relative positions of grip plate 44 and grip body 46.

During testing, tensile and compressive loads are applied by actuator 30 once the sample has been raised to the testing temperature. Extensometer assembly 42 measures the resulting change in the length of the sample. Hydrostatic bearing 24 accurately maintains the position of actuator rod 26, because it is near grip 28. Grips 22, 28 provide better than 1% alignment for the sample, permitting ceramic samples to be accurately axially loaded in both tension and compression.

OTHER EMBODIMENTS

Other embodiments of the invention are within the scope of the claims.

What is claimed is:

1. Apparatus for testing comprising:
load means for applying tensile and compressive loads, said load means comprising a loading component, and
a grip connected to said load means, said grip comprising
a grip plate having means for engaging the end of an elongated sample having a longitudinal axis,
a grip body having one end connected to said grip plate and another end connected to said loading component, said loading component having a load axis,
concentricity adjustment means for lockably adjusting the concentricity of said plate with respect to said body, and
angle adjustment means for lockably adjusting the angle of said plate with respect to said body,
whereby, when said end of said sample is engaged by said plate, said longitudinal axis and said load axis can be aligned with respect to concentricity and angle, locked in place and maintained in alignment during tensile and compressive testing by said concentricity adjustment means and said angle adjustment means.

2. The apparatus of claim 1 wherein said concentricity adjustment means comprises pairs of opposed adjustment bolts each threadedly mounted on said body and having an end bearing against said plate, said bolts being mounted along axes in a plane perpendicular to said load axis.

3. The apparatus of claim 1 wherein said angle adjustment means comprises a plurality of bolts connecting said plate to said body along axes having a component parallel to load axis.

4. The apparatus of claim 3 further comprising a plurality of locking bolts between said body and said plate along said load axis for providing force between said plate and said body opposite to that provided by said plurality of bolts.

5. The apparatus of claim 1 wherein said end of said sample sits in wedge pieces and is pushed along said load axis by a piston carried by said grip body in a piston chamber in said grip body.

6. The apparatus of claim 5 wherein said piston carries a hemispherically-shaped piece mounted for limited rotation in a hemispherically-shaped recess on the end of said piston, said piece having a bearing surface for pushing against said end of said sample.

7. The apparatus of claim 5 wherein there are a plurality of wedge pieces the outer surfaces of which form together a conical outer shape, said wedge pieces being mounted in and bearing against a conical recess in said grip plate, said pieces having interior surfaces conforming to the outer shape of said end of said sample.

8. The apparatus of claim 5 in which there are pressure chambers defined by said body on both sides of said piston.

9. The apparatus of claim 5 further comprising withdrawing members in passages in said body and connected to said wedge pieces, permitting said wedge pieces to be withdrawn during attachment of said sample.

10. The grip of claim 1 wherein said load means further comprises a load cell and a threaded stud connecting said body to said load cell.

11. A material testing load frame comprising:

a pair of columns, a table between said columns, a crosshead between said columns and above said table to define a testing region between said columns, table and crosshead, an actuator connected to said table for applying tensile and compressive loads along a load axis, a load cell connected to said crosshead for transmitting tensile and compressive loads along a load axis, a pair of grips connected to said load cell and actuator, at least one said grip comprising a grip plate having means for engaging the end of an elongated sample having a longitudinal axis, a grip body having one end for connecting to said grip plate and another end connected to said load cell or said actuator, concentricity adjustment means for lockably adjusting the concentricity of said plate with respect to said body, and angle adjustment means for lockably adjusting the angle of said plate with respect to said body, whereby, when said end of said sample is engaged by said plate, said longitudinal axis and said load axis can be aligned with respect to concentricity and angle, locked in place and maintained in alignment during tensile and compressive testing by said concentricity adjustment means and said angle adjustment means.

12. The load frame of claim 11 wherein said concentricity adjustment means comprises pairs of opposed adjustment bolts each threadedly mounted on said body and having an end bearing against said plate, said bolts being mounted along axes in a plane perpendicular to said load axis.

13. The load frame of claim 11 wherein said angle adjustment means comprises a plurality of bolts connecting said plate to said body along axes having a component parallel to load axis.

14. The load frame of claim 13 further comprising a plurality of locking bolts between said body and said plate along said load axis for providing force between said plate and said body opposite to that provided by said plurality of bolts.

15. The load frame of claim 11 wherein said end of said sample sits in wedge pieces and is pushed along said load axis by a piston carried by said grip body in a piston chamber in said grip body.

16. The load frame of claim 15 wherein said piston carries a hemispherically-shaped piece mounted for limited rotation in a hemispherically-shaped recess on the end of said piston, said piece having a bearing surface for pushing against said end of said sample.

17. The load frame of claim 15 wherein there are a plurality of wedge pieces the outer surfaces of which form together a conical outer shape, said wedge pieces being mounted in and bearing against a conical recess in said grip plate, said pieces having interior surfaces conforming to the outer shape of said end of said sample.

18. The load frame of claim 15 in which there are pressure chambers defined by said body on both sides of said piston.

19. The load frame of claim 15 further comprising withdrawing members in passages in said body and connected to said wedge pieces, permitting said wedge pieces to be withdrawn during attachment of said sample.

20. The load frame of claim 11 further comprising a threaded stud connecting said body to said load cell.

21. The load frame of claim 11 wherein said actuator has a portion mounted below said table and an actuator rod passing upward through a hole in said table and further comprising a hydrostatic bearing through which said actuator rod passes.

22. The load frame of claim 11 wherein both said grips have said grip body, grip plate, concentricity adjustment means and angle adjustment means.

* * * * *